(12) United States Patent
Rodriguez Lelis et al.

(10) Patent No.: US 8,585,644 B2
(45) Date of Patent: Nov. 19, 2013

(54) PERIPHERAL INTRAVENOUS SAFETY CATHETER WITH QUICK, PAINLESS PUNCTURE SYSTEM

(75) Inventors: Jose Maria Rodriguez Lelis, Emiliano Zapata (MX); Jose Antonio Arellano Cabrera, Emiliano Zapata (MX); Maria Teresa Lucas Jimenez, Emiliano Zapata (MX); Alfredo Chalita Vizcarra, Emiliano Zapata (MX); Hugo Solorzano Quiroz, Emiliano Zapata (MX); Rocio Cassaigne Hernandez, Emiliano Zapata (MX)

(73) Assignee: Equipos Medicos Vizcarra, S.A., Morelos (MX)

( * ) Notice: Subject to any disclaimer, the term of this patent is extended or adjusted under 35 U.S.C. 154(b) by 0 days.

(21) Appl. No.: 13/560,434

(22) Filed: Jul. 27, 2012

(65) Prior Publication Data
US 2013/0150784 A1 Jun. 13, 2013

(30) Foreign Application Priority Data
Dec. 12, 2011 (MX) ...................... MXA2011013382

(51) Int. Cl.
*A61M 5/50* (2006.01)
(52) U.S. Cl.
USPC ..................................... 604/110; 604/164.01

(58) Field of Classification Search
USPC .......... 604/110, 164.01, 164.04, 164.08, 192, 604/197, 158, 272
See application file for complete search history.

(56) References Cited

U.S. PATENT DOCUMENTS

2007/0270753 A1* 11/2007 Kulli ......................... 604/164.01
2011/0306933 A1* 12/2011 Djordjevic et al. ...... 604/164.08

* cited by examiner

*Primary Examiner* — Quynh-Nhu H Vu
(74) *Attorney, Agent, or Firm* — Novak Druce Connolly Bove + Quigg LLP

(57) ABSTRACT

A Peripheral Intravenous Safety Catheter with Quick, Painless Puncture System (PISCQPPS) and a cannula with a retractile needle mounted in a manually operated bellows mechanism to prevent re-use, avoid accidental perforation and ensure safe disposal. This PISCQPPS offers the advantages of reducing or eliminating pain; reducing the possibility of multiple perforation; reducing the need for experience and technical know-how in the matter of injection; being fitted with a safety system; and easy to use. The PISCQPPS consists of two sequential operating systems-namely, a painless insertion system that is located inside a case, consisting of a catheter, a catheter holder, a trigger guard, a trigger-guard holder, a catheter-holder tube, a cannula, a cannula holder, a spring, a filter holder, and a filter; along with a safety system inside whose case the cannula holder, the cannula and the bellows all operate at the same time.

20 Claims, 9 Drawing Sheets

PERIPHERAL INTRAVENOUS SAFETY CATHETER WITH QUICK, PAINLESS PUNCTURE SYSTEM

CROSS REFERENCE TO RELATED APPLICATIONS

This application claims priority under 35 U.S.C. §119 to Application No. MX/a/2011/013382 filed in Mexico on Dec. 12, 2011, the entire contents of which are hereby incorporated by reference.

FIELD OF THE INVENTION

This invention is related to the hospital-equipment manufacturing industry, and more specifically to the industry that manufactures instruments for venous puncturing and canalization. Even more specifically, it is linked to the industry that manufactures instruments for quick puncturing and canalization that reduce or eliminate pain.

BACKGROUND OF THE INVENTION

As mentioned by Rivera, et al. [1], intravenous (IV) therapy springs from the need to transfer blood from one human being to another, and dates from around 1492. Currently, catheter-insertion devices are common; when a catheter is inserted in a patient in order to administer a liquid intravenously, a disposable needle is used that passes through a catheter to puncture a vein and enable the probe to enter. Subsequently, the needle is withdrawn, leaving the catheter in place so that it can be connected to an intravenous bag or bottle, or to a tip for later use.

There is epidemiological evidence, worldwide, that the main unease regarding mishaps in the use of perforating instruments and their later disposal as a part of infectious hospital waste relates to possible transmission of the AIDS virus and, more often, of the hepatitis-B and hepatitis-C viruses, due to lesions caused by needles that are contaminated with human blood. Hence, new products have been designed incorporating special coverings for the needle, or mechanisms for withdrawing the latter into a protective chamber. Such devices are, for example, described in U.S. Pat. Nos. 4,747,831, 4,828,548, 5,129,884, 5,501,675, 5,817,058, 5,989,220, 7,771,394 and 7,740,615. Many of the devices described in the aforesaid patents consist of numerous parts that substantially drive up their manufacturing costs, as well as hampering the user's ability to feel whether the needle is correctly inserted into the patient. Other devices need to be operated with two hands, or their needles are liable to become prematurely withdrawn during transportation, storage or handling.

Furthermore, studies [2] show that the pain associated with the penetration of the skin by the needle is caused by friction and the thrust load that occurs when the needle is inserted. Davis [3] states that there is only one relevant factor that affects the forces that occur when the skin is penetrated—i.e. the ratio between the force of the insertion and the surface area of the point. It should be added that pain—which is a mechanism for protecting the organism and occurs whenever tissue is being damaged, making the individual react in order to eliminate the painful stimulus—has been divided into two types—fast and slow. The former type is produced within around 0.1 seconds of receiving the stimulus, also being described as penetrating, stabbing, sharp, acute, electric, etc. For example, such pain is felt when a needle is stuck into the skin or when the latter is cut with a knife, though no quick, pulsing pain is felt in most of the deeper body tissues.

Since we know that venous canalization is currently carried out manually in patients, the staff who perform this operation must be very experienced and employ a special, highly polished technique in order to avoid hurting and harming the patient when they insert the needle into the vein. However, despite such experience and skill, the patient can sometimes be subjected to pain and multiple skin punctures when an appropriate vein cannot be found or due to bad insertion techniques. Some attempts have been made to produce devices aimed at reducing or doing away with pain by improving injection techniques or eliminating the need for such specialized techniques—e.g. the Auxiliary Device for Painless Venous Perforation (Spanish initials: DAPV), patented in Cuba in 1966, and the Device for Procuring Painless Peripheral Venous Catheterization (Mexican patent number: 247215).

The first of these devices, the DAPV, is a type of "crossbow" in which a plastic syringe is mounted along with its plunger and needle, which is shot into the selected vein by means of a mechanism that is triggered one single time by the technician carrying out the process.

The second of them, the Device for Procuring Painless Peripheral Venous Catheterization, consists of a mounting framework for the mechanisms for supporting, attaching and triggering catheters or hypodermic needles, with both patents permitting the uncontrolled shooting of the said catheters or hypodermic needles.

As can be inferred from this text, an intravenous catheter device must have certain qualities, including the ability to: (a) reduce or eliminate pain; (b) reduce the chances of multiple skin punctures; (c) reduce the need for special injection skills and experience, in addition to which it must: (d) be fitted with a safety system and (e) be easy to use, and these are the features that this invention claims to have.

AIMS OF THE INVENTION

The main aim of the invention is to provide a device that permits fast, pain-reducing perforation and canalization.

Another of its aims is to reduce human error at the moment of perforation, thus avoiding the need for multiple perforations and reducing the risk of passing all the way through the vein.

Yet another aim is to reduce the need for experienced catheterizing staff and diminish the risk of contamination with body fluids, in addition to all the other aims that will become clear upon perusal of this text and the illustrative, though not exhaustive, drawings that accompany it.

BRIEF DESCRIPTION OF THE INVENTION

This invention consists of a system for inserting intravenous catheters, and above all of a system for doing this quickly in a way that will reduce or do away with pain by means of a retractable cannula mounted in a manually operated bellows-type mechanism to prevent repeated use and incorrect perforation and allow for safe disposal.

The system in question is a double one, one of whose components permits fast penetration so as to prevent pain and avoid stretching of the vein during cutting. A second component contains a manual safety mechanism that enables the contaminated cannula to be gathered inside a protective chamber so as to prevent the user or other people from coming into contact with it after use, thus preventing accidental perforation and the transmission of diseases.

Furthermore, the fast-perforation system reduces the number of incidences of repeat perforation due to inexperience, since the system itself does the perforation, also reducing the fear of a vein being perforated all the way through or severed, by controlling the depth of penetration.

Likewise, the retractile system assures that there is no contact whatsoever with the cannula after placement of the catheter, allowing the said cannula to be removed to a safe distance inside the security system.

The propulsion mechanism consists of a spring that passes through a cannula-carrying device inside a catheter holder that is itself supported by a safety device to prevent accidental triggering. When the device is loaded, these elements are stored inside a case and the trigger-guard mechanisms, which stick out through some slits in the said case, keep them pressed down. When the two halves of the guards are pressed in towards the middle, two things happen: first two half-slits come together to form a single slit, through which part of the catheter-holding tube passes, reaching a given length depending on how far the spring is stretched, upon which the spring, being liberated by the movement of the two halves of the trigger-guard, pushes the cannula holder, which, in turn, pushes the catheter-holding tube. This movement enables the vein to be perforated very fast, and, also, when the catheter-holding tube is liberated, the safety-catch holder is also freed, which, after perforation, can be deployed to cover the cannula holder and part of the cannula, since the end of the said cannula is normally covered by the catheter-holding tube.

The bellows mechanism is stretched, in order to cover the part of the cannula that came into contact with human tissue and/or blood, by holding the cannula holder apart from the cannula and pulling the socket towards the end opposite to the one where the cannula holder is located.

DETAILED DESCRIPTION OF THE INVENTION

This detailed description is supported by illustrations of the preferred variant of the invention.

Figure 1:
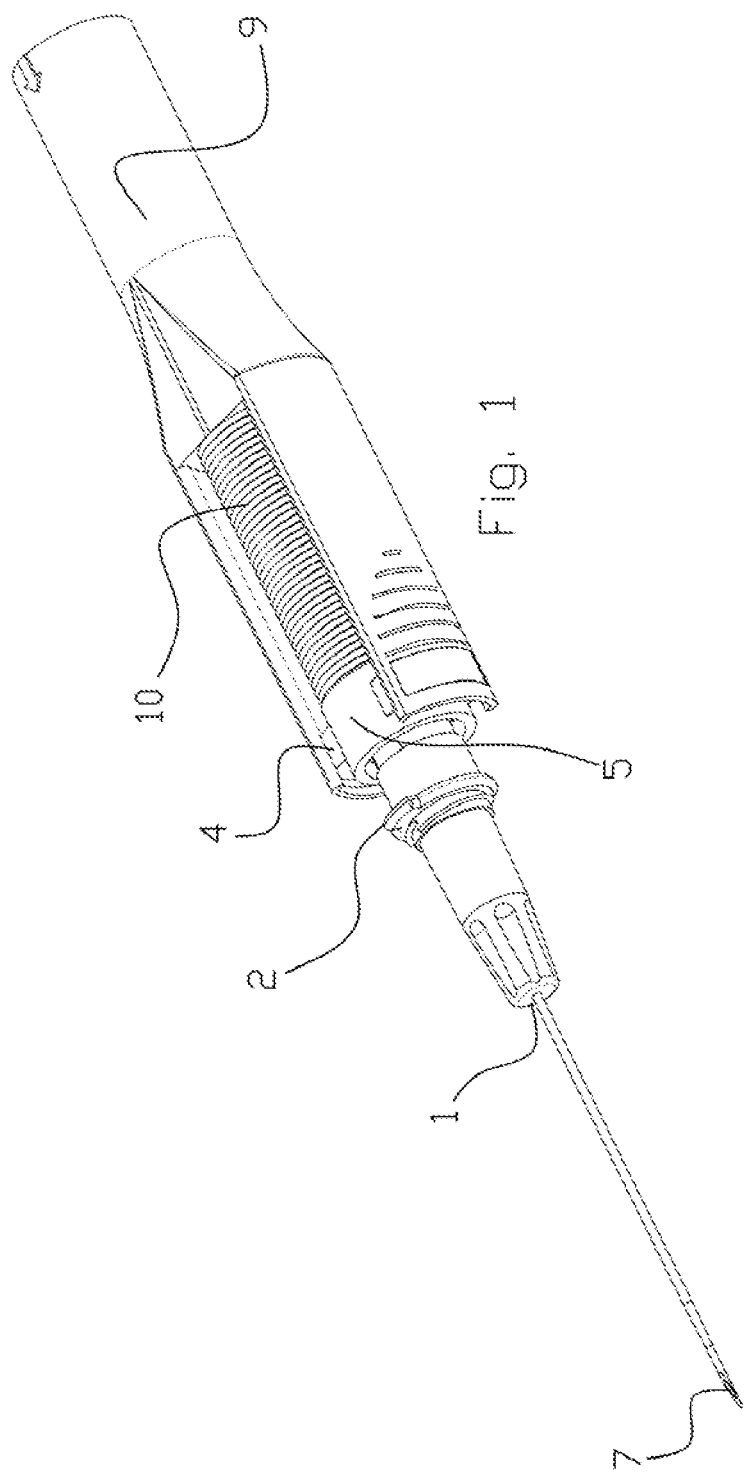
FIG. 1 is an isometric depiction of the Peripheral Intravenous Safety Catheter with Quick, Painless Puncture System (initials: PISCQPPS).

FIG. 1 is an isometric depiction of the Peripheral Intravenous Safety Catheter with Quick, Painless Puncture System (PISCQPPS). The catheter (1) surrounds the cannula (7). The cannula-catheter assemblage is attached to the catheter holder (3), which is located in the trigger holder (5) from which the triggers (4) protrude. The bellows section is located inside the case (9).

Figure 2:
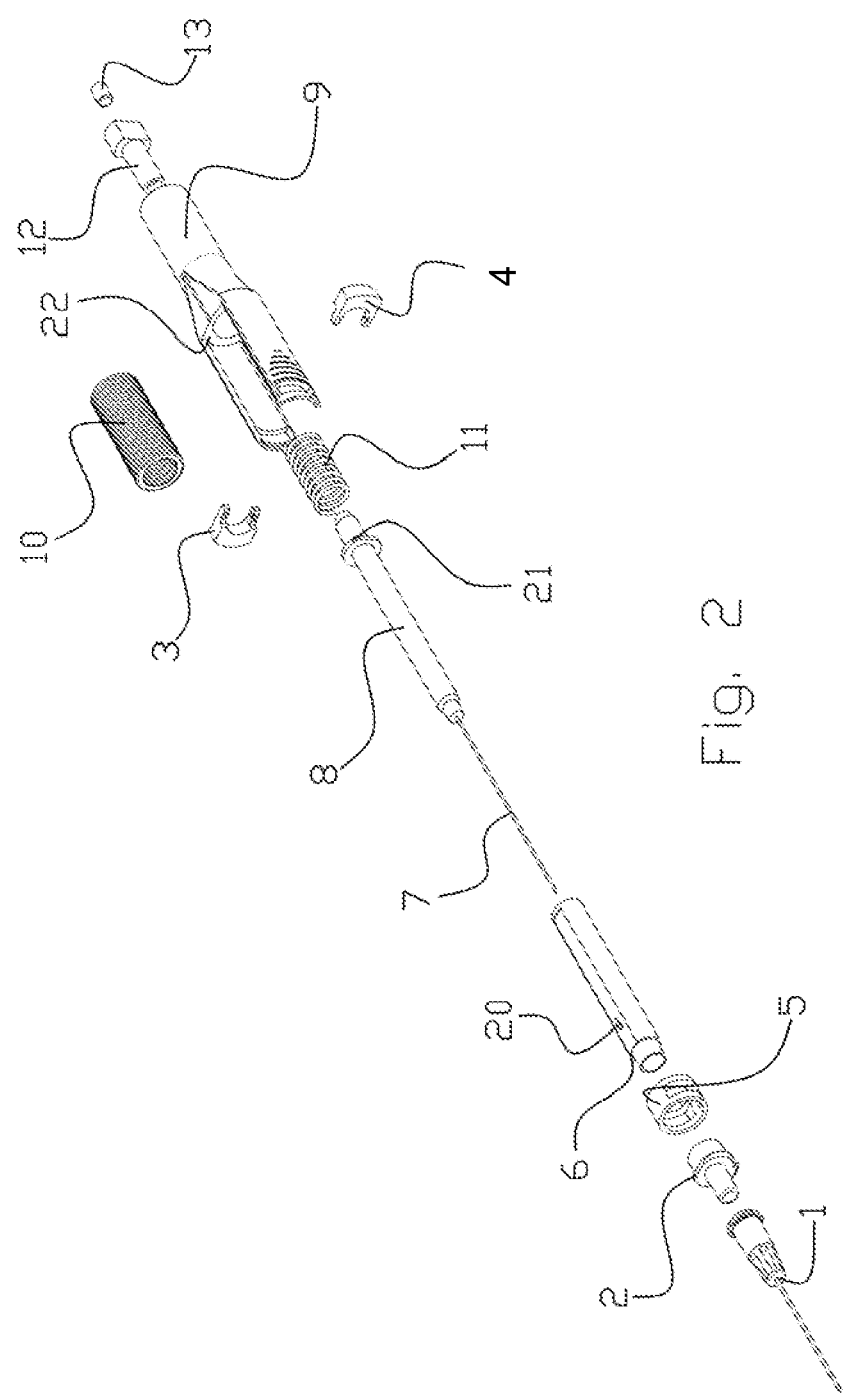
FIG. 2 is an exploded diagram showing the parts that make up the Peripheral Intravenous Safety Catheter with Quick, Painless Puncture System.

The PISCQPPS therefore consists of 9 parts, as shown in the exploded view in FIG. 2. As can be seen from the said FIG. 2, the parts that make up the PISCQPPS are: (1) the catheter; (2) the catheter holder; (3) and (4) the trigger guard, (5) the trigger-guard case; (6) the tube that holds the catheter; (7) the cannula; (8) the cannula holder; (9) the case; (10) the bellows; (11) the spring; (12) the filter holder; and (13) the filter.

Figure 3:
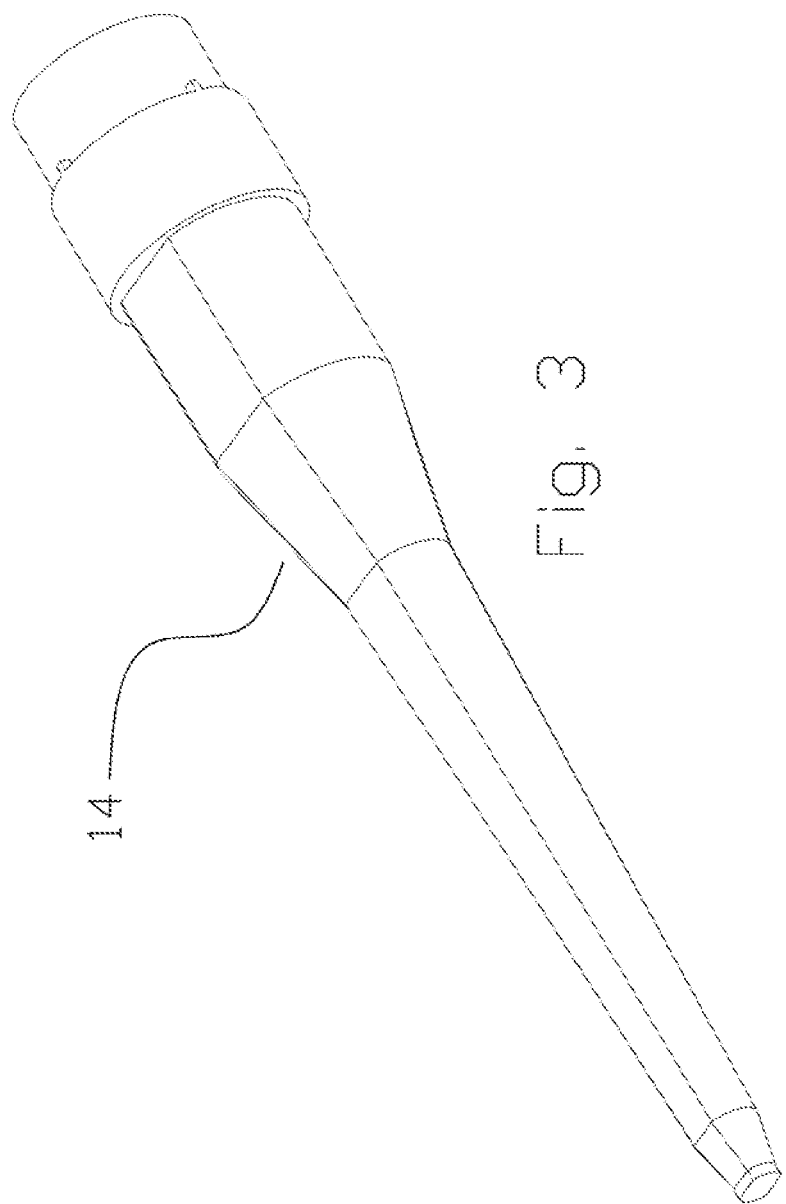
FIG. 3 is a detailed drawing of the protective cap of the PISCQPPS.
Figure 4:
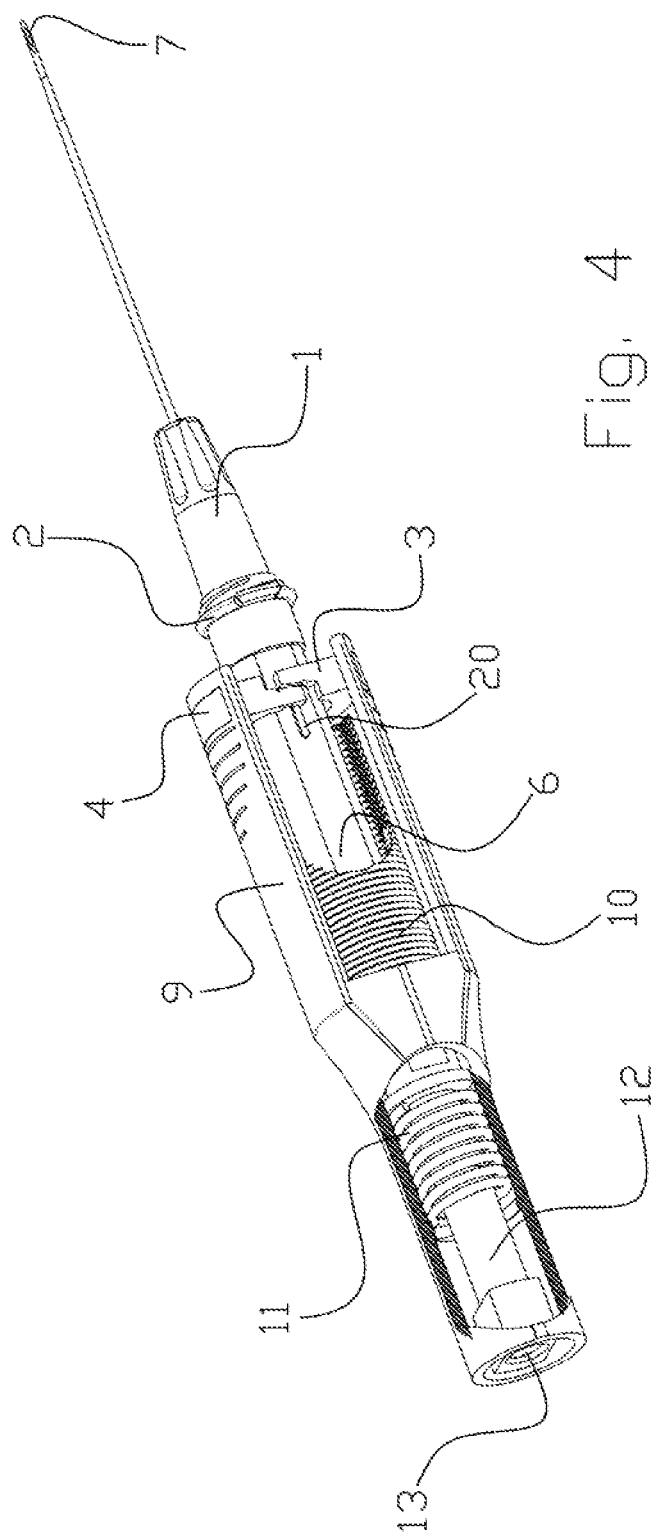
FIG. 4 shows the firing system in detail.

As shown in FIG. 14, the PISCQPPS can be carried inside its cap (14), which is designed to protect it during transportation and prevent the needle from touching anything until it is used. When the top is removed, the PISCQPPS is bared ready for perforation. Once the said PISCQPPS is in the right position for perforation, the case (9) and the triggers (3) and (4) are pressed simultaneously, as shown in FIG. 3, thus activating the painless puncture system.

Figure 5:
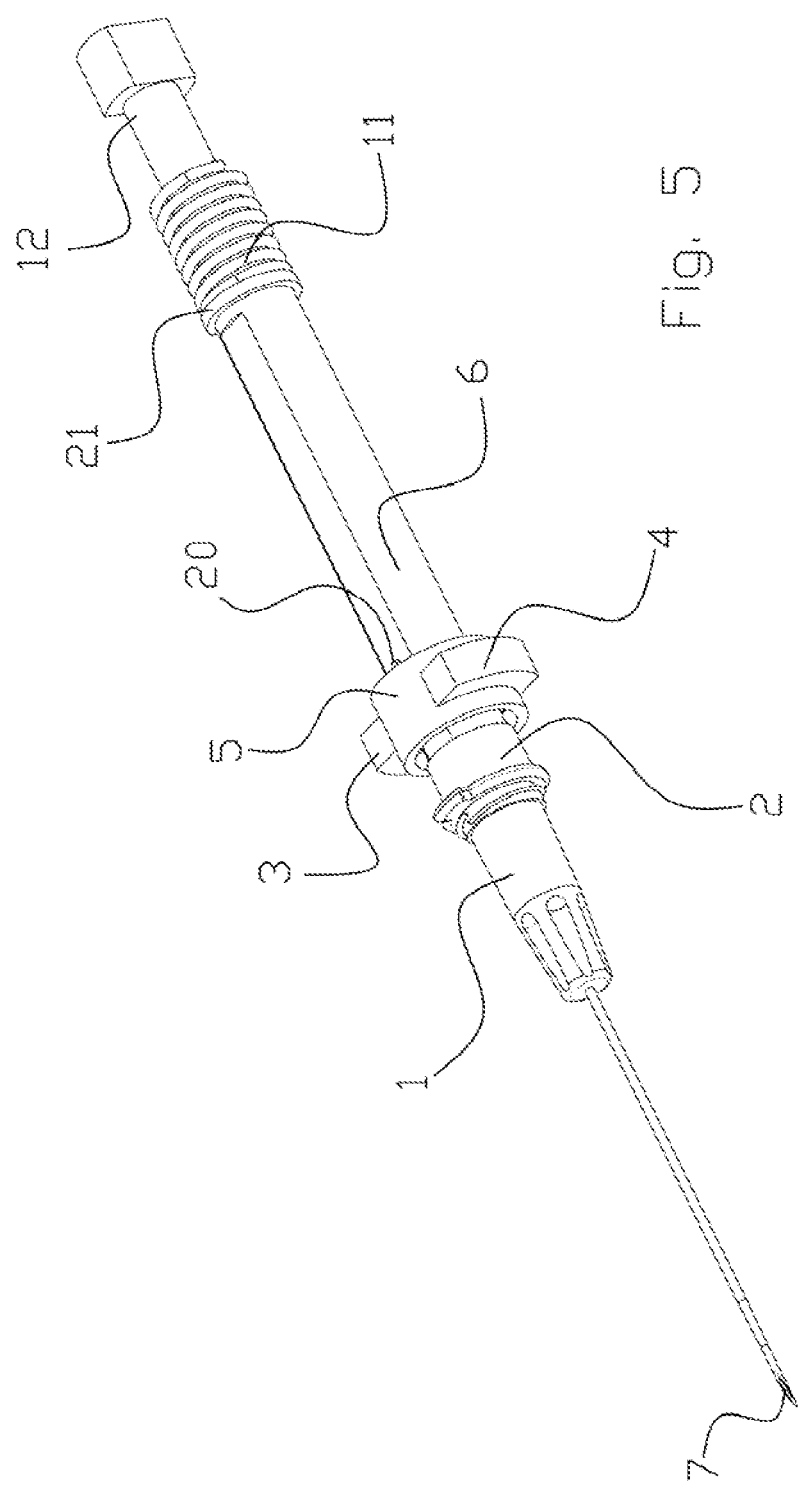
FIG. 5 is a drawing of the painless puncture system, showing its parts, how they interact with each other, and where they are located vis-à-vis each other.

The painless puncture system, shown in FIG. 5, is located inside the case (9), being composed of (1) the catheter; (2) the catheter case; (3) and (4) the trigger guard; (5) the guard holder; (6) the catheter-holding tube; (7) the cannula; (8) the cannula holder; (11) the spring; (12) the filter holder; and (13) the filter. When triggers (3) and (4) are activated, they move inside the catch holder (5), bringing the bevel of the catheter holder (6) into line with the trigger slit. When the said slit and the bevel are aligned, the high-speed spring (11) action frees the catheter (1), the catheter holder (2), the catheter-holding tube (6), the cannula (7), the cannula holder (8), the filter holder (12) and the filter (13) as a single body.

These parts move a distance that is predetermined based on experience and the average thicknesses of the different skin layers, penetrating the skin and vein proper.

Figure 6:
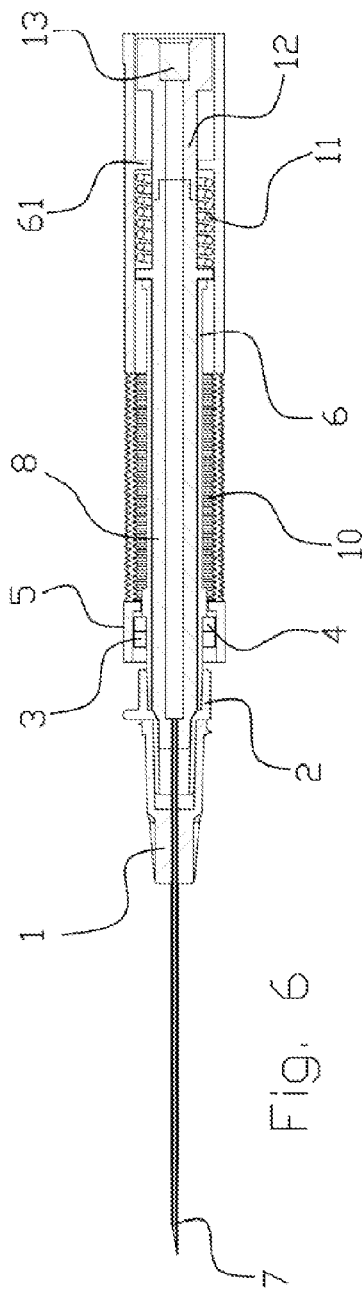
FIG. 6 is an A-A section showing the safety system.
Figure 7:
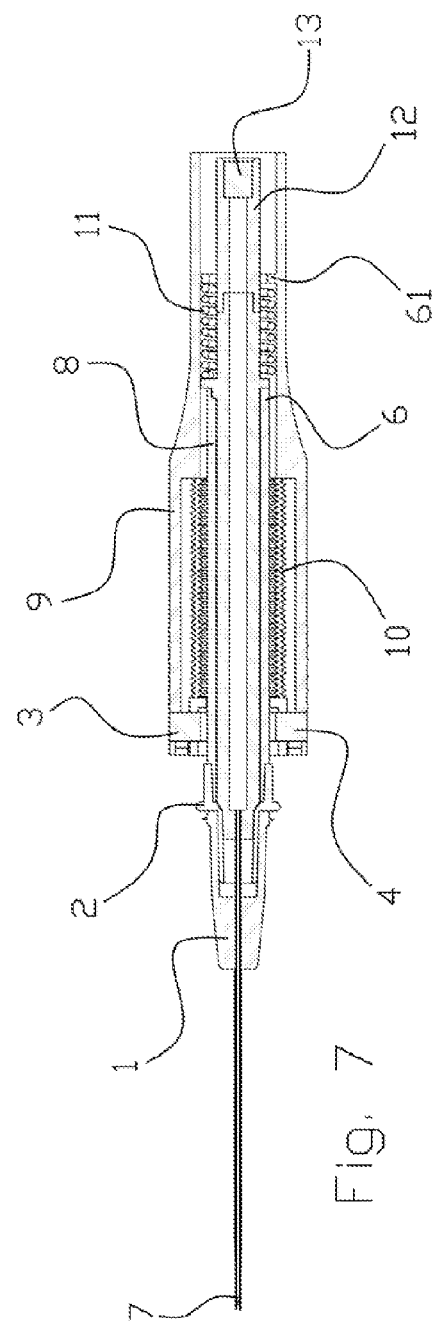
FIG. 7 is a B-B section of the safety system.
Figure 11:
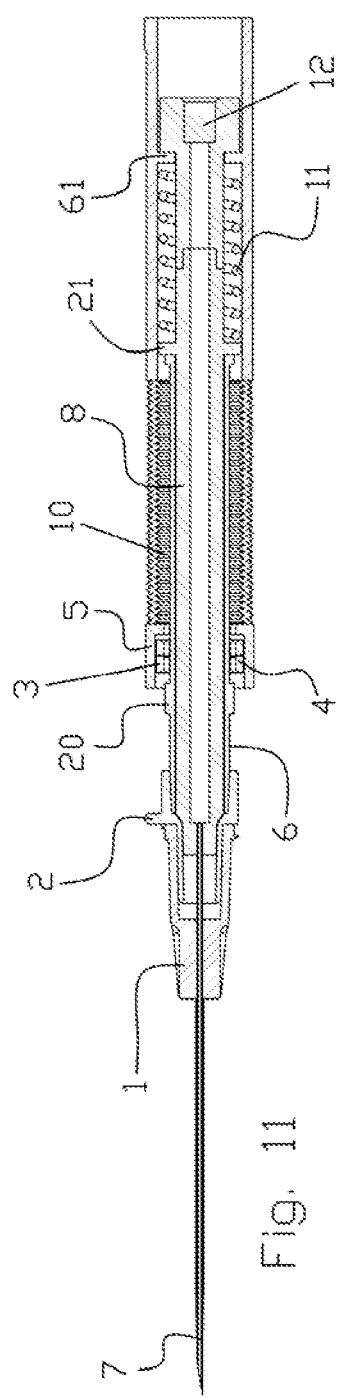
FIG. 11 shows the position of the parts after the trigger has been activated.
Figure 12:
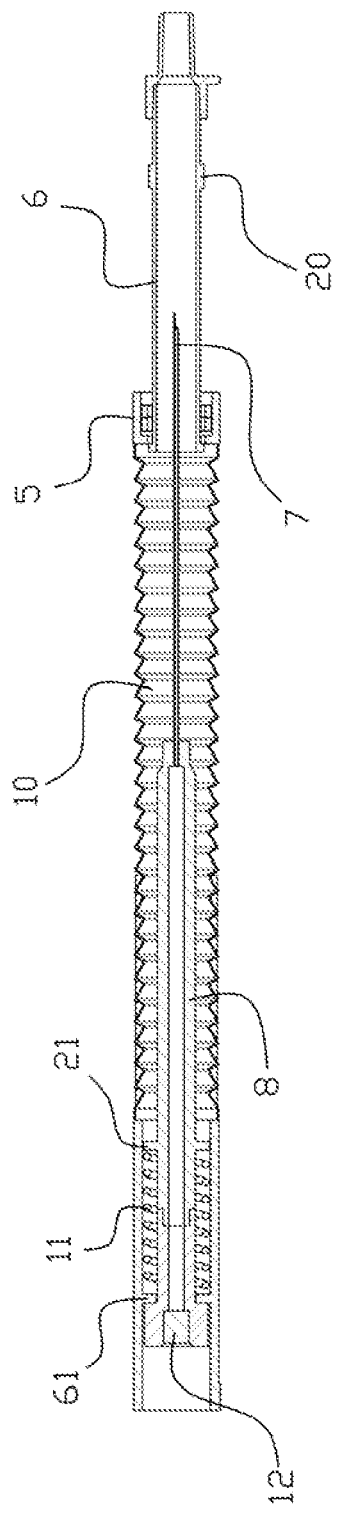
FIG. 12 shows how the bellows section is elongated to cover the cannula and prevent the user from having any contact with it.

Once the catheter (1) has penetrated the skin and vein, with the parts of the PISCQPPS being in the positions shown in FIG. 11, the said PISCQPPS is placed in its final position following approved medical procedures, being slightly separated from the catheter holder (2), and, using the cannula for support, the catheter is inserted until it reaches its final position, at which point the safety system shown in FIGS. 6 and 7 —in which the case (9), the cannula holder (8), the cannula (7) and the bellows (10) spring into action simultaneously—is triggered. The spring (11) is inside this system, but does not play an active role until the catheter holder (2) and the catheter-holding tube (4), which are conjoined like a single piece, are held down and the case (9) is pulled down, activating the bellows and pulling the cannula holder (8) and the cannula (7) backwards, so that the PISCQPPS adopts the position shown in FIGS. 6 and 7, with the case (9), the cannula holder (8), the cannula (7) and the bellows (10) moving simultaneously. The spring (11) is inside this system but does not play an active role, only starting to function when the catheter holder (2) and the catheter-holder tube (4), conjoined as if they were a single entity, are held down and the said case (9) is pulled so as to activate the bellows and pull the cannula holder (8) and the cannula (7) backwards, with the result that the PISCQPPS adopts the position shown FIG. 12.

In the course of this process, the cannula (7), which is attached to the cannula holder, is protected inside the catheter-holder tube (6) and the bellows (10), which, when the process is finished, is fully extended so as to form a protective chamber. Once the cannula has been thus protected, it can be subjected to hazardous waste disposal procedures without risk of any accidental contact with it occurring.

Figure 8:
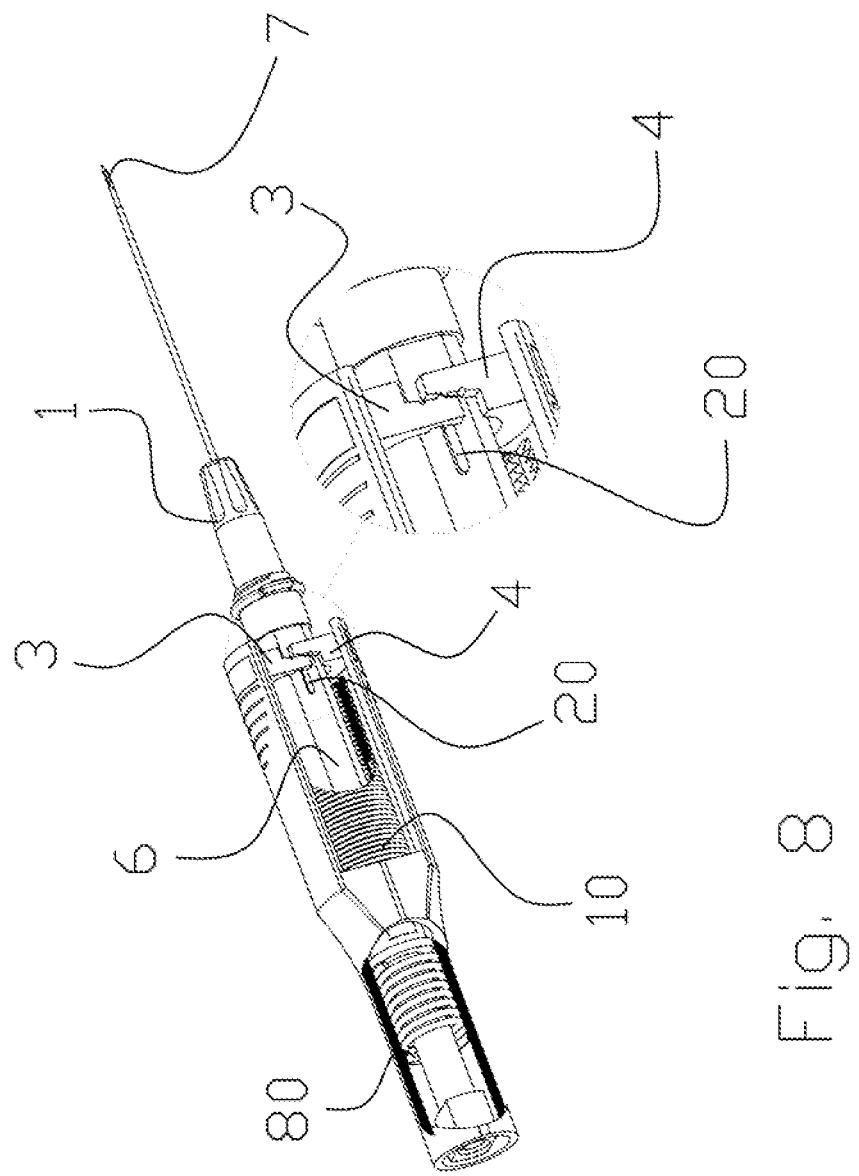
FIG. 8 shows the Peripheral Intravenous Safety Catheter with Quick, Painless Puncture System, depicting the position of the safety guard in detail.
Figure 10:
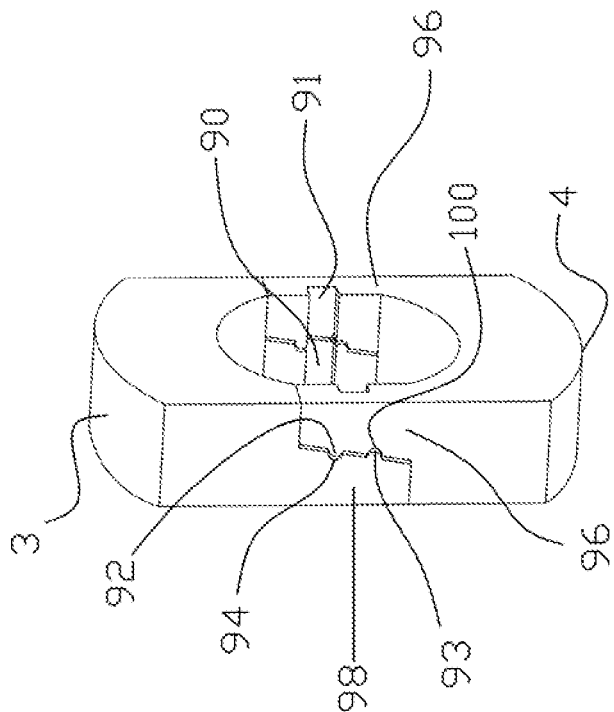
FIG. 10 shows the trigger guard after activation.
Figure 9:
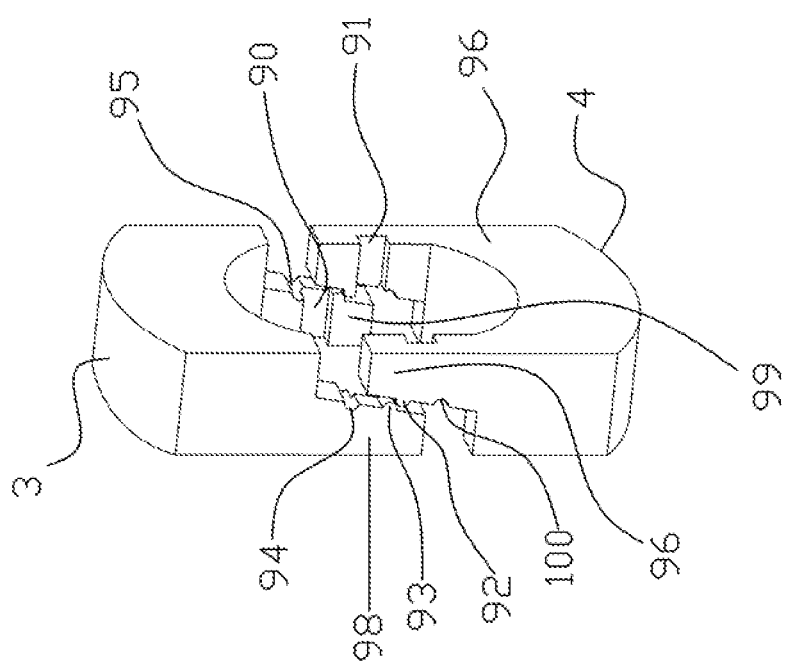
FIG. 9 shows the trigger before it is activated.

The firing system is basically activated by moving triggers (3) and (4) inside the trigger holder (5) that is shown in detail in FIG. 8. This is a simple, innovative triggering system (See FIG. 9) whereby two pieces, each with a sloping contact surface, can slide against each other so as to create an open slot through which the mechanism that is to be freed can pass. The outer surface of each of the aforesaid pieces has a ridge that prevents the system from being activated accidentally, with the said system only being set in motion when enough pressure is applied to move it all the way, as shown in FIG. 9*b*.

In other words, the two halves of the trigger guard (3 and 4) are separate pieces with hollow semicircular channels that join together to form a complete transversal cavity inside which the distal tip of the catheter-holder tube (6) will be housed with its projecting ridge (20), which, when the two halves of the trigger guard are displaced, jams against one of the surfaces of one of the said halves. At one of its ends, each half of the trigger guard has various pairs of legs (96). These legs (96) each have four surfaces—i.e. the one that forms the transversal cavity, the outer front one the inner front one, and the side one—and, rather than covering the whole area of the upper surfaces of the sides, they cover half of the upper side of each half of the trigger guard. The shapes of the five exposed faces of the legs come together to form a channel or slit (91 and 90) and the corresponding slots in front of it, so as to form certain limits with jutting out parts (93) and slits (90) that keep the trigger guard in the same position, without any change, unless a force of a certain magnitude is applied at a certain point and in a certain direction so as to activate the two halves of the said trigger guard.

On the inner surface of legs 96, 98 and 99 of each half of the trigger guard are slits 95 and 94, which move limit 92, and its counterpart on the other leg, into the triggering position. Limit 93 and its counterpart on the other leg of the same half of the trigger guard move into place when the trigger catch in slot 100 is activated along with its counterpart on the other leg located on the same half.

References

[1.] A. M. Rivera, K. W. Strauss, A. Van Zundert, and E. Mortier, The history of peripheral intravenous catheters: How little plastic tubes revolutionized medicine, Acta Anaesth. Belg., 2005, 56, 271-282

[2.] Hiroyuki Kataoka, "Measurement of the tip and friction force acting on a needle during penetration", National Institute of Advanced Industrial Science and Technology, MICCAI '02 Proceedings of the 5th International Conference on Medical Image Computing and Computer-Assisted Intervention-Part I, 2002

[3.] Davis, S. P., "Hollow microneedles for molecular transport across skin", Ph.D. Thesis, Georgia Institute of Technology, 2003.

The invention has been described in sufficient detail to enable anybody with a modicum of knowledge on the topic to duplicate the results mentioned above. However, though any person skilled in the technique pertaining to the invention described here would be able to make modifications that are not described in this application, nonetheless, if the information that is set forth in the following claims is necessary in order to apply the said modifications to a given structure, or to the process for manufacturing the said structure, then the structure in question must be deemed to form a part of the invention here described.

The invention claimed is:

1. Peripheral Intravenous Safety Catheter with Quick, Painless Puncture System (PISCQPPS), characterized as comprising: a catheter connected to the catheter holder that is located in the trigger holder that also holds the trigger guard, made up of two halves; the section consisting of the catheter and the catheter-holder is connected, via the said catheter holder, to the catheter-holder tube; the cannula is located inside the catheter, the catheter holder and the catheter-holder tube; at the tip opposite to the free one, the cannula is attached to the cannula holder, while most of the PISCQPPS is located inside the case; between the case and the cannula holder is the bellows, while a spring is located at the distal end of the cannula holder in order to propel it at high speed when the cannula-holder spring is released; before being activated, the halves of catches have been moved along in such a way that the halves of the front and back slits do not match each other and, when the trigger guard has not been activated, the longitudinal ridges of the catheter-holder tube are pressed up against the corresponding areas of the one of the halves of the guard.

2. As claimed in claim 1, the Peripheral Intravenous Safety Catheter with Quick, Painless Puncture System (PISCQPPS, which is also distinguished by the fact that both halves of the trigger guard have a pair of legs, of which the ones on the side, the ones on the outside and the contact ones have four faces, while the central ones bear half of the slits that allow the longitudinal ridges of the catheter-holder tube to pass through when the trigger guard is activated, while the slanted contact surfaces have slits and limits that allow the trigger guard to be held in place unless a certain amount of force, with certain point of leverage and a certain orientation, is exercised in order to slide the contact surfaces to a point where the ridges or limits meet the corresponding slits in the firing position.

3. Peripheral Intravenous Safety Catheter with Quick, Painless Puncture System (PISCQPPS), which, as claimed in claim 1, is also distinguished by the fact that it has a filter carrier, with a filter at the entrance to the catheter to prevent extraneous materials from entering the said catheter.

4. Peripheral Intravenous Safety Catheter with Quick, Painless Puncture System (PISCQPPS), which, as claimed in claim 1, is distinguished by the fact that it also has a protective cap or sheath to protect both it and those who might come into contact with it during transportation.

5. Peripheral Intravenous Safety Catheter with Quick, Painless Puncture System (PISCQPPS), which, as claimed in claim 1, is distinguished by the fact that part of the catheter, the catheter holder, the trigger guard, the trigger-guard holder, the catheter-holder tube, the cannula, the cannula holder, the spring, the filter holder and the filter are all located inside the case.

6. Peripheral Intravenous Safety Catheter with Quick, Painless Puncture System (PISCQPPS), which, as claimed in claim 1, is distinguished by its possession of a safety system in which the case, the cannula-holder tube, the cannula and the bellows all work simultaneously.

7. Peripheral Intravenous Safety Catheter with Quick, Painless Puncture System (PISCQPPS), which, as claimed in claim 2, is also distinguished by the fact that it has a filter carrier, with a filter at the entrance to the catheter to prevent extraneous materials from entering the said catheter.

8. Peripheral Intravenous Safety Catheter with Quick, Painless Puncture System (PISCQPPS), which, as claimed in claim 2, is distinguished by the fact that it also has a protective cap or sheath to protect both it and those who might come into contact with it during transportation.

9. Peripheral Intravenous Safety Catheter with Quick, Painless Puncture System (PISCQPPS), which, claimed in claim 2, is distinguished by the fact that part of the catheter, the catheter holder, the trigger guard, the trigger-guard holder, the catheter-holder tube, the cannula, the cannula holder, the spring, the filter holder and the filter are all located inside the case.

10. Peripheral Intravenous Safety Catheter with Quick, Painless Puncture System (PISCQPPS), which, claimed in claim 3, is distinguished by the fact that part of the catheter, the catheter holder, the trigger guard, the trigger-guard holder, the catheter-holder tube, the cannula, the cannula holder, the spring, the filter holder and the filter are all located inside the case.

11. Peripheral Intravenous Safety Catheter with Quick, Painless Puncture System (PISCQPPS), which, claimed in claim 4, is distinguished by the fact that part of the catheter, the catheter holder, the trigger guard, the trigger-guard holder, the catheter-holder tube, the cannula, the cannula holder, the spring, the filter holder and the filter are all located inside the case.

12. Peripheral Intravenous Safety Catheter with Quick, Painless Puncture System (PISCQPPS), which, claimed in claim 7, is distinguished by the fact that part of the catheter, the catheter holder, the trigger guard, the trigger-guard holder, the catheter-holder tube, the cannula, the cannula holder, the spring, the filter holder and the filter are all located inside the case.

13. Peripheral Intravenous Safety Catheter with Quick, Painless Puncture System (PISCQPPS), which, claimed in claim 8, is distinguished by the fact that part of the catheter, the catheter holder, the trigger guard, the trigger-guard holder, the catheter-holder tube, the cannula, the cannula holder, the spring, the filter holder and the filter are all located inside the case.

14. Peripheral Intravenous Safety Catheter with Quick, Painless Puncture System (PISCQPPS), which, as claimed in claim 2, is distinguished by its possession of a safety system in which the case, the cannula-holder tube, the cannula and the bellows all work simultaneously.

15. Peripheral Intravenous Safety Catheter with Quick, Painless Puncture System (PISCQPPS), which, as claimed in claim 3, is distinguished by its possession of a safety system in which the case, the cannula-holder tube, the cannula and the bellows all work simultaneously.

16. Peripheral Intravenous Safety Catheter with Quick, Painless Puncture System (PISCQPPS), which, as claimed in claim 4, is distinguished by its possession of a safety system in which the case, the cannula-holder tube, the cannula and the bellows all work simultaneously.

17. Peripheral Intravenous Safety Catheter with Quick, Painless Puncture System (PISCQPPS), which, as claimed in claim 5, is distinguished by its possession of a safety system in which the case, the cannula-holder tube, the cannula and the bellows all work simultaneously.

18. Peripheral Intravenous Safety Catheter with Quick, Painless Puncture System (PISCQPPS), which, as claimed in claim 7, is distinguished by its possession of a safety system in which the case, the cannula-holder tube, the cannula and the bellows all work simultaneously.

19. Peripheral Intravenous Safety Catheter with Quick, Painless Puncture System (PISCQPPS), which, as claimed in claim 8, is distinguished by its possession of a safety system in which the case, the cannula-holder tube, the cannula and the bellows all work simultaneously.

20. Peripheral Intravenous Safety Catheter with Quick, Painless Puncture System (PISCQPPS), which, as claimed in claim 9, is distinguished by its possession of a safety system in which the case, the cannula-holder tube, the cannula and the bellows all work simultaneously.

* * * * *